United States Patent [19]
Nitta et al.

[11] Patent Number: 5,643,744
[45] Date of Patent: Jul. 1, 1997

[54] METHOD FOR PRODUCING POLYPEPTIDE

[75] Inventors: Itaru Nitta, Tokyo; Takuya Ueda, Chiba; Kimitsuna Watanabe, Tokyo, all of Japan

[73] Assignee: Sumitomo Chemical Company, Limited, Osaka, Japan

[21] Appl. No.: 317,356

[22] Filed: Oct. 4, 1994

[30] Foreign Application Priority Data

| Oct. 4, 1993 | [JP] | Japan | 5-248168 |
| Mar. 4, 1994 | [JP] | Japan | 6-034834 |
| Mar. 4, 1994 | [JP] | Japan | 6-034835 |
| May 17, 1994 | [JP] | Japan | 6-102861 |
| May 17, 1994 | [JP] | Japan | 6-102862 |

[51] Int. Cl.$^6$ .............. C12N 15/00; C12N 1/00; C12P 21/00; C12Q 1/68
[52] U.S. Cl. ............ 435/68.1; 435/69.1; 435/71.1; 435/317.1; 435/849; 435/6
[58] Field of Search ............ 435/68.1, 69.1, 435/71.1, 71.2, 172.3, 70.1, 317.1, 849, 6; 935/33, 88

[56] References Cited

U.S. PATENT DOCUMENTS 4,440,676  4/1984  Cadogan et al. .

FOREIGN PATENT DOCUMENTS

| 0302442 | 8/1988 | European Pat. Off. . |
| 64-27493 | 1/1989 | Japan . |
| 4-200390 | 7/1992 | Japan . |
| 8808453 | 11/1988 | WIPO . |

*Primary Examiner*—Robert A. Wax
*Assistant Examiner*—Tekchand Saidha
*Attorney, Agent, or Firm*—Birch, Stewart, Kolasch & Birch, LLP

[57] ABSTRACT

The present invention provides a method for producing a polypeptide, which comprises condensing precursors comprising an amino acid and an adaptor in the presence of ribosomes, rRNAs, a larger ribosomal subunit or ribosomal proteins, and an aromatic tertiary amine.

14 Claims, No Drawings

METHOD FOR PRODUCING POLYPEPTIDE

BACKGROUND OF THE INVENTION

1. Field of the Invention

The present invention relates to a method for producing polypeptides.

2. Description of the Related Art

As a method for producing polypeptide in the cell-free translation system, there has been known a method which required ribosomes, chemical energy sources such as ATP and GTP, and soluble protein factors.

However, the method was not always satisfactory in that the method required energy sources and soluble protein factors. Therefore, the conventional method was so complicated that it was not practical for producing polypeptide.

Under the circumstances, the present inventors have intensively studied the method for producing polypeptides in the cell-free translation system, and have found that the condensation of a precursor comprising amino acids and adaptors can be effectively performed in the absence of the energy source such as ATP and GTP, and soluble protein factors but in the presence of ribosomes and an aromatic tertiary amine.

SUMMARY OF THE INVENTION

Thus, the present invention provides a method for producing a polypeptide, which comprises condensing precursors comprising an amino acid and an adaptor in the presence of ribosomes, rRNAs, a larger ribosomal subunit or ribosomal proteins, and an aromatic tertiary amine.

It also provides a method for producing a polypeptide, which comprises the steps of;

(a) reacting an amino acid with an adaptor molecule in the presence of aminoacyl-tRNA synthetase to obtain a precursor comprising an amino acid and a nucleic acid adaptor; and (b) condensing the precursors in the presence of ribosomes, rRNAs, a larger ribosomal subunit or ribosomal proteins, and in the presence of an aromatic tertiary amine.

DETAILED DESCRIPTION OF THE PREFERRED EMBODIMENT

According to the present invention, the condensation of precursors comprising an amino acid and an adaptor can be effectively carried out without energy source such as ATP and GTP and soluble protein factors but in the presence of ribosomes and an aromatic tertiary amine.

First, description will be made on the method for producing a polypeptide, which comprises condensing precursors comprising an amino acid and an adaptor in the presence of ribosomes, rRNAs, a larger ribosomal subunit or ribosomal proteins, and in the presence of an aromatic tertiary amine.

The condensation reaction of the precursors is usually carried out in the presence of ribosomes, rRNAs, a larger ribosomal subunit or ribosomal proteins, and in the presence of an aromatic tertiary amine.

The ribosomes, the rRNA, the larger ribosomal subunit or the ribosomal proteins to be used in the present reaction are obtained by a conventional method such as extraction from cell organs or organisms which can be obtained from nature or purchased.

The ribosomes of the E. coil are obtained by the following procedures. For example, E. Coil cells are mixed with a buffer solution and crushed with a mortar or pressed by a French press to give a suspension, which is then subjected to ultracentrifugation to give a supernatant. Then the supernatant is separated by centrifugation to give the ribosomes of E. coil. Furthermore, the larger ribosomal subunit and the ribosomal proteins can be obtained by the known sucrose density gradient method.

The organisms which may be eucaryote or procaryote include, for example, mammals, insects, plants such as algae, mosses, fern, gymnosperm, angiosperm, fungi, bacteria, molds and yeasts. Preferable examples of the organisms are: mammals including rat, mouse, cow and goat; algae including green algae and blue-green algae; angiosperm including wheat, rice, tobacco, tomato and the like; bacteria including Escherichia., Bacillus., Pseudomonas and the like; molds including Neurospora, Aspergillus, Penicillium and the like; and yeasts including Saccharomyces and the like.

Thermophilic bacteria such as *Bacillus strearothermophilus*, aquiatucus and *Thermus thermophilus* which are not only resistant to high temperature but also less sensitive to denaturation by an organic solvent are preferably used as the source of the ribosomes, the rRNA, the larger ribosomal subunit or the ribosomal proteins.

As the cell organs such as mitochondria and chloroplast may be exemplified.

The ribosomes washed with an aqueous cation solution of high concentration may be used in the present invention. The extraction of the ribosomal protein is carried out by conventional methods such as described in "Ribosomes and Protein Synthesis A practical Approach (G. Spedding, Oxford University Press, 1990)".

The aromatic tertiary amine compounds to be used in the present process include pyridine compounds, imidazole compounds, purine base compounds and pyrimidine base compounds.

The pyridine compounds to be used in the present method can be represented by the formula I:

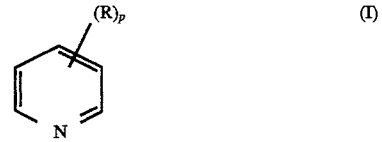

wherein R independently represents a member selected from the group of a hydrogen atom, a halogen atom, a $C_1$–$C_4$ aliphatic hydrocarbon group, an amino group, a $C_5$–$C_8$ alicyclic hydrocarbon group, a $C_6$–$C_{10}$ aromatic hydrocarbon group, a hydroxyl group, a sulfhydryl group and a heterocyclic group having at least one heteroatom, all of which except the hydrogen atom and the halogen atom may be optionally substituted; alternatively R represents a group of the formula: —COO, wherein Q represents a hydrogen atom, a $C_1$–$C_4$ aliphatic hydrocarbon group, an amino group, a $C_5$–$C_8$ alicyclic hydrocarbon group, a $C_6$–$C_{10}$ aromatic hydrocarbon group, a hydroxyl group, a sulfhydryl group or a heterocyclic group having at least one heteroatom, all the groups of which may be optionally substituted; and p represents an integer of 1 to 5.

The imidazole compounds to be used in the present method may be represented by the formula II:

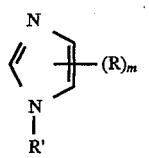

(II)

wherein R is the same as defined above; R' represents the same atoms or groups as those given in R provided that it excludes a halogen atom, an amino group, a hydroxyl group and a sulfhydryl group, and those atom and groups are also excluded in Q; R and R' are independent from each other; and m represents an integer of 1 to 3.

The purine base compounds include a compound represented by the formula III:

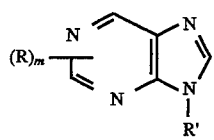

(III)

wherein R and R' are the same as defined above and independent from each other; and m represents an integer of 1 to 3, and a compound of the formula IV:

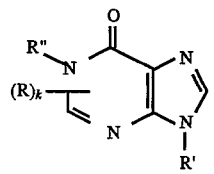

(IV)

wherein R and R' are the same as defined above, R" represents the same atoms or groups with those given in R provided that it excludes a halogen atom, an amino group, a hydroxyl group and a sulfhydryl group, and those atom and groups are also excluded in Q; R, R' and R" are independent from each other; and k represents an integer of 1 or 2.

The pyrimidine base compounds include a compound represented by the formula V:

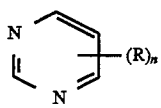

(V)

wherein R is the same as defined above and n represents an integer of 1 to 4;

a compound of the formula VI:

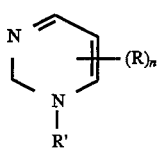

(VI)

wherein R, R' and n are the same as defined above and R and R' are independent from each other; and a compound of the formula VII:

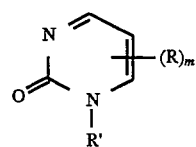

(VII)

wherein R and R' are the same as defined above and independent from each other, and m represents an integer of 1 to 3.

In the chemical formulae I to VII above, examples of the $C_1$–$C_4$ aliphatic hydrocarbon group for R, R' and R" are a methyl group, an ethyl group, a n-propyl group, an isopropyl group, a n-butyl group, a sec.-butyl group, an isobutyl group and a tert.-butyl group.

Examples of the $C_5$–$C_8$ alicyclic hydrocarbon group are a cyclopentyl group, a cyclohexyl group, a cycloheptyl group and a cyclooctyl group.

Examples of the $C_6$–$C_{10}$ aromatic hydrocarbon group are a phenyl group and a naphthyl group.

Examples of the halogen atom are a fluorine atom, a chlorine atom, a bromine atom and an iodine atom.

Examples of the heteroatom in the heterocyclic group are an oxygen atom, a nitrogen atom or a sulfur atom. Examples of the heterocyclic group having at least one heteroatom which group may be optionally substituted are a ribosyl group, a deoxyribosyl group and monophosphate, phosphodiester and triphosphate derivative thereof.

Examples of the pyridine compound are α-picoline, β-picoline, γ-picoline, 2-aminopyridine, 3-aminopyridine, 4-aminopyridine and 4-dimethylaminopyridine.

Examples of the imidazole compound are imidazole and 1-methylimidazole.

Examples of the purine base compound are guanine, purine, adenine, 9-methyladenine, 7-methyladenine, adenosine, 2'-deoxyadenosine, adenosine 5'-monophosphate, adenosine 5'-diphosphate and guanosinetriphosphate.

Examples of the pyrimidine base compound are cytosine, uracil, thymine, cytidine, 2'-deoxycytidine, cytidyl 5'-monophosphate and cytidyl 5'-diphosphate. However, the aromatic tertiary amines are not limited thereto.

The concentration of the aromatic tertiary amine is not specified and the preferable concentration of the aromatic tertiary amine varies according to the kinds of the base.

However, the preferable concentration of the aromatic tertiary amine is usually within the range of from the saturation concentration in water to $1/10^9$ or preferably $1/10^6$ of the saturation concentration in water. For example, the preferable concentration for pyridine, pyrimidine or imidazole is 10 nM to about 10M; 1 nM to about 1M for purine, 2-aminopyridine, 4-aminopyridine or 4-dimethylaminopyridine; 100 pM to about 100 mM for adenosine 5'-diphosphate or cytidyl 5'-diphosphate; and 10 pM to about 10 mM for adenine or guanine.

The pH of the condensation reaction solvent is not specified, however, it is preferably 5 to 11, more preferably 6 to 10 in terms of the yield.

The present condensation reaction is preferably carried out in the presence of appropriate cations such as a magnesium ion and at least one ion selected from a potassium ion and an ammonium ion to allow the condensation reaction to moved more efficiently.

The concentration of the potassium ion or ammonium ion is preferably 50 mM to 500 nM, more preferably 100 mM to 300 mM. As for the concentration of the magnesium ion, it is preferably 1 mM to 500 mM, more preferably 5 mM to 300 mM.

A metal ion such as a zinc ion, an iron ion, a copper ion or a manganese ion may be added to accelerate the condensation reaction.

The reaction temperature is usually 0° to 90° C. When the ribosomes of a highly thermophilous bacteria are used, the reaction can be carried out at the range of 30° to 90° C. When the ribosomes of a thermophilic bacteria are used, the reaction temperature is preferably 30° to 80° C. When other ribosomes are used, the reaction temperature is preferably 30° to 70° C., more preferably 30° to 60° C.

The present condensation reaction may be conducted in the presence of other additives to accelerate the condensation reaction. Examples of such additives include polyamines such as spermine and spermidine, polyethylene glycols, glyrerols and alcohols.

The present reaction is preferably conducted in the presence of a template molecule comprising a nucleic acid which interacts with the adaptor molecules.

Examples of such a template molecule include an mRNA of interest or the derivatives thereof that is present in living cells or an mRNA obtained by synthetic or enzymatic methods. Furthermore, a compound such as polyuridylic acid (poly(U)), polyadenylic acid (poly(A)) or a block copolymer thereof (e.g., poly(UA)) that represents the synthetic functions of the mRNA may also be used as the template.

A nucleic acid coding for a useful protein may be also used as the template. Examples of the useful proteins are a biologically active peptide such as human growth hormones, protein pharmaceuticals, proteins involved in antigen-antibody reaction and enzymes that catalyze biological processes.

The precursors comprising amino acids and adaptors include an aminoacyl-tRNA, which is usually obtained by reacting an amino acid with the tRNA molecule as the adaptor in the presence of aminoacyl-tRNA synthetase or may be chemically synthesized from an amino acid and a corresponding adaptor.

The amino acids to be used in the present invention may be a compound having a carboxylic acid group and an amino group in the same molecule and may also be a naturally occurring or non-naturally occurring type. The carbon atom to which the amino group is bonded may be at any position of the carbon chain to which the carboxylic acid group is bonded, and the number of the amino groups and the carboxylic acid groups present in the molecule is not limited. When the said amino acids possess a chiral center, they include an L-amino acid, a D-amino acid and a racemic mixture thereof.

Examples of the amino acid to be used in the present method are: protein constituent (naturally occurring) amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine and derivatives thereof; β-alanine, γ-aminobutyric acid, 5-aminolevulinic acid and derivatives thereof, all of which are present in living cells; and amino acids that do not exist in the living cells such as p-, m- or o-aminobeozoic acid.

Examples of adaptors include nucleic acids such as tRNAs (for example, those described in G. Fasman, ed, "Handbook of Biochemistry and Molecular Biology" 3rd Ed., Vol 2, p. 423 CRR press (1975), and D. H. Gauss, M. Sprizl, Nucleic Acids Res, 9, r1 (1981)) or a variant thereof that can be specifically combined to the corresponding amino acids which are present in living cells or obtainable by an enzymatic or synthetic methods.

The reaction of the adaptor with the amino acid is, for example, carried out in the presence of the aminoacyl-tRNA synthetase, which can be obtained by such a method as described in "Seikagaku Jikken Koza", vol. 7, Chapter 1, Edited by Biochemical society of Japan, 1975.

The reaction may be also conducted by a synthetic method.

The reaction of the adaptors with the amino acids may be, for example, carried out in a single reaction vessel or in separate reaction vessels for each of the amino acids at about 37° C.

Then the solution is supplied for the subsequent condensation reaction while the concentrations of the reactants are adjusted to specified concentrations, if necessary.

After the precursor such as an aminoacyl-tRNA is obtained, it can be recovered from the reaction mixture and then supplied to the condensation reaction.

After completion of the reaction, the polypeptide can be obtained by a conventional post-treatment.

Next, the present invention wild be explained in detail by the following examples, however, it is not construed to limit the present invention thereto.

EXAMPLE 1

A solution of 5 mM $MgCl_2$, 10 mM KCl, 2 mM ATP, 5 μCi/ml (L)-[$^{14}$C]Phenylalanine and 3.0 $A_{280}$/ml aminoacyl-tRNA synthetase (the designation expresses the concentration of the aminoacyl-tRNA synthetase with an absorbance value at 280 nm for 1 ml of the solution ), which was obtained from the cell extract solution of E. coil A19, in 200 μl was prepared. The extraction of the enzyme was carried out according to the method described in "Seikagaku Jikken Koza", vol. 7, Chapter 1, Edited by Biochemical society of Japan, 1975.

The resultant reaction mixture was allowed to react at 37° C for 5 min to obtain a phenylalanyl-tRNA (which will be referred to as "[$^{14}$C]Phenylalanyl-tRNA or Phe-tRNA$^{Phe}$" hereinafter) as the precursor for condensation. Then the [$^{14}$C]Phenylalanyl-tRNA was recovered after phenol extraction using a centrifugal concentration (Microcon-10, Amicon; 12,000 rpm, at 0° C., for 1 hr, three times). The final stock buffer contained 37.5 μg/ml(1,500 cpm/μl) Phe-tRNA$^{Phe}$, 20 mM NaOAc (pH 4.5) and 5 mM $MgCl_2$.

Next, a solution of 15 mM $MgCl_2$, 120 mM KCl and 16 $A_{260}$/ml ribosomes derived from E. coil A19 in 25 μl was prepared using 1 μl of the Phe-tRNA$^{Phe}$ solution obtained above (two replicate). The preparation method was in accordance with that described in "Ribosomes and Protein Synthesis A Practical Approach" (G. Spedding, Oxford University Press, 1990).

One of the solutions prepared above was made an aqueous 50% pyridine solution, and then allowed to react at 37° C. for 60 min to give polyphenylalanine Then 10 μl of water and 1 μl of 1N potassium hydroxide were added to the reaction solution and the reaction mixture was allowed to react at 37° C. for 60 min to hydrolyze the unreacted Phe-tRNA$^{Phe}$.

The aliquots of the obtained reaction solution were subjected to the thin layer chromatography on a silica-plate (Silica-Gel 60, Merck) using a solvent system of 1-butanol/water/acetic acid=4/1/1 and visualized by an imaging analyzer (BAS 2000 made by Fuji Photo Film Co., Ltd.)

After 12 hours, the [$^{14}$C]polyphenylalanine was identified by the Rf value of exceeding 0.58, which corresponds to that of an authentic trimer sample.

It has been found that the obtained polyphenylalanine is a polypeptide composed of more than ten amino acids by the HPLC(high performance liquid chromatography) analysis.

When the ribosomes were absent in the present reaction system, the condensation reaction did not take place.

EXAMPLE 2

The reaction was carried out in a similar manner to that in the Example 1 but using Thermus thermophilus, HB 27 in place of the E. coil, and yielded polyphenylalanine.

EXAMPLE 3

The reaction was carried out in a similar manner to that in the Example 1 but using Thermus thermophilus, HB 27 in place of the E. coil at 60° C., and yielded polyphenylalanine.

EXAMPLE 4

Ribosomes obtained from the E. coil was subjected to centrifugation using 10%–20% sucrose density gradient to separate the larger subunit and the smaller subunit. Among the obtained subunits, only the larger subunit could effectively produce polyphenylalanine as in the Example 1.

EXAMPLE 5

Ribosomes obtained from the E. coli was contacted with phenols to remove the protein to yield the ribosomal RNA and the condensation reaction was carried out in the presence of the ribosomal RNA and in a similar manner to that in the Example 1, and yielded polyphenylalanine.

EXAMPLE 6

Ribosomes were digested by 1 mg/ml of the proteinase K in the presence of 0.5% sodium dodecyl sulfate at 37° C. for 1 hour to remove the ribosomal protein. The condensation reaction was carried out in the presence of the rRNA in place of the ribosomes and in a similar manner to that in the Example 1, and yielded polyphenylalanine.

EXAMPLE 7

In this example, 0.4 mg/ml polyuridylic acid made by Sigma Corp was used as the template while other reaction conditions were the same as in the Example 1.

After completion of the reaction, the aliquots of the obtained reaction solution were subjected to the thin layer chromatography on a silica-plate(Silica-Gel 60, Merck) using a solvent system of 1-butanol/water/acetic acid=4/1/1 and visualized by an imaging analyzer (BAS 2000 made by Fuji Photo Film Co., Ltd.)

After 12 hours, the [$^{14}$C]polyphenylalanine was identified by the Rf value of exceeding 0.58.

When the ribosomes or the puvine was absent in the present reaction system, the condensation reaction did not take place.

EXAMPLE 8–19

In these examples the condensation reactions were carried out in a similar manner to that in the Example 7 except that the concentrations of the magnesium ion and the potassium ion were varied as shown in the following Table 1. The yield of polyphenylalanine was calculated based on the intensity of the radioactivity.

TABLE 1

| Example No. | Magnesium ion (mM) | Potassium ion (mM) | Yield (%) |
| --- | --- | --- | --- |
| 8 | 0.6 | 120 | 73.2 |
| 9 | 5.6 | 120 | 75.6 |
| 10 | 10.6 | 120 | 70.3 |
| 11 | 15.6 | 120 | 66.7 |
| 12 | 20.6 | 120 | 68.6 |
| 13 | 50.6 | 120 | 65.1 |
| 14 | 100.6 | 120 | 51.1 |
| 15 | 15.6 | 52 | 9.9 |
| 16 | 15.6 | 122 | 66.7 |
| 17 | 15.6 | 242 | 75.0 |
| 18 | 15.6 | 502 | 73.8 |
| 19 | 15.6 | 802 | 62.3 |

EXAMPLE 20–26

In these examples the condensation reactions were carried out as in the Example 7 except that the reaction temperature was varied as shown in the following Table 2. The yield of the polyphenylalanine was calculated based on the intensity of the radioactivity.

TABLE 2

| Example No. | Temperature (°C.) | Yield (%) |
| --- | --- | --- |
| 21 | 0 | 22.6 |
| 22 | 15 | 24.6 |
| 23 | 30 | 68.9 |
| 24 | 37 | 69.3 |
| 25 | 50 | 74.2 |
| 26 | 60 | 71.2 |
| 27 | 80 | 31.7 |

EXAMPLE 27–33

In these examples the condensation reactions were carried out in a similar manner to that in the Example 7 except that the concentration of the (pyridine) was varied as shown in the following Table 3. The yield of the polyphenylalanine was calculated based on the intensity of the radioactivity.

TABLE 3

| Example No. | Concentration of pyridine (V %) | Yield (%) |
| --- | --- | --- |
| 27 | 70 | 10.0 |
| 28 | 65 | 25.8 |
| 29 | 60 | 33.9 |
| 30 | 55 | 60.2 |
| 31 | 50 | 69.5 |
| 32 | 40 | 45.0 |
| 33 | 30 | 9.5 |
| Control | 0 | 2.0 |

EXAMPLE 34

In this example the condensation reaction was carried out in a similar manner to that in the Example 7 except that a ribosomal RNA obtained by removing proteins from the whole ribosome using phenol or the like was used in place of the whole ribosomes derived from the E. coil, and yielded polyphenylalanine.

EXAMPLE 35

Using phenylalanine and lysine, block copolymeric ribonucleic acid represented by the formula:

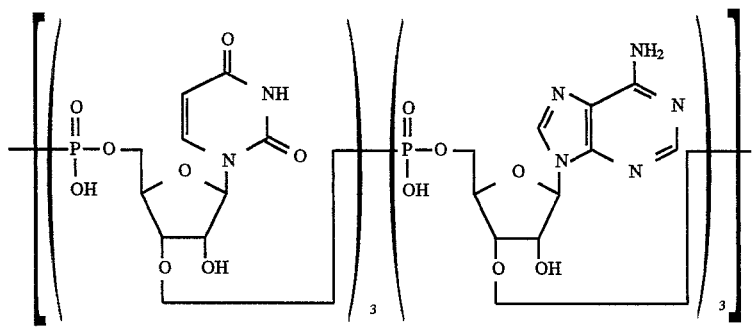

as the template and the whole ribosome, a subunit thereof or rRNA, which are obtained from *E. coil* or thermophilous bacterium, the condensation reactions are carried out in a similar manner to that in the Example 7.

An alternate copolymer with highly regulated coordination comprising the repeating unit structure:

—(—Phe—Lys—)— was produced.

EXAMPLE 36–47

In these examples the reactions were carried out in a similar manner to that in the Example 7 except that the concentrations of the magnesium and potassium ions were adjusted to 200 mM, the reaction time was adjusted to 12 hours, and the concentrations of the aromatic tertiary amine were adjusted to the specified concentrations listed in the following Table 4.

Table 4 shows the results of the experiments where the pyridines, imidazoles, purine bases and pyrimidines were used and it also provides the yield of polyphenylalanine.

TABLE 4

| Example | Concentration (mM) | | | | | |
|---|---|---|---|---|---|---|
| | (100.0 | 50.0 | 10.0 | 5.0 | 1.0 | 0.2) |
| | YIELD (%) | | | | | |
| 36 4-Dimethylamino-pyridine | 13.7 | 14.1 | 17.1 | 16.9 | | |
| 37 4-Aminopyridine | 13.7 | 13.0 | 17.6 | 17.6 | | |
| 38 2-Aminopyridine | 24.6 | 20.4 | 17.0 | 15.9 | | |
| 39 Imidazole | 13.8 | 12.3 | 8.8 | 9.4 | | |
| 40 1-Methylimidazole | 8.8 | 8.8 | 7.7 | 6.9 | | |
| 41 Purine | 26.3 | 26.3 | 21.2 | 18.2 | | |
| 42 Adenine | | | | 19.9 | 16.8 | 10.7 |
| 43 Adenosine | | 19.8 | 18.4 | 18.6 | 6.6 | |
| 44 2'-Deoxyadenosine | | 18.4 | 18.0 | 15.7 | 8.8 | |
| 45 Adenosine 5'-phosphate | | 12.6 | 12.5 | 11.9 | 9.6 | |
| 46 Pyrimidine | 17.5 | 17.6 | 18.1 | 18.1 | | |
| 47 Cytosine | | | 15.3 | 14.2 | 11.7 | 10.6 |

EXAMPLE 48

Ribosomes were digested by 1 mg/ml of the proteinase K in the presence of 0.5 % sodium dodecyl sulfate at 37° C. for 1 hour to remove the ribosomal protein. Thus obtained rRNA was used in place of the ribosomes to produce polyphenylalanine in a similar manner to that in the Example 7, which yielded polyphenylalanine.

EXAMPLE 49

In this example a highly thermophilic bacterial (*Thermus thermophilus*, HB 27) was used in place of the *E. coil* in the Example 7, which yielded polyphenylalanine.

EXAMPLE 50

Polylysine was produced from lysine using ribosomes of *E. coil* as in the Example 7 or using ribosomes of thermophilic bacterial (*Thermus thermophilus*, HB 27) as in the Example 49 and the polyadenilyic acid as the template.

EXAMPLE 51

The dihydrofolic acid reductase was produced from the twenty natural amino acids using an RNA coding for the dihydrofolic acid reductase as the template while other reaction conditions were the same as employed in the Example 7.

EXAMPLE 52

The ribosomes obtained from the *E. coil* were subjected to centrifugation using 10%–20% sucrose density gradient to separate the larger subunit and the smaller subunit. Among the obtained subunits, the larger subunit was effective for producing polyphenylalanine when used in place of the ribosomes used in the Example 7.

What is claimed is:

1. An in vitro method for producing a polypeptide, which comprises:

condensing, in an aqueous solution, precursors comprising an amino acid and a nucleic acid adaptor which comprises tRNA in the presence of an effective amount of ribosomes or a larger ribosomal subunit, and an effective amount of an aromatic tertiary amine under conditions which allow for the production of a polypeptide, wherein substantially all of soluble protein factors are removed from the aqueous solution and where the condensing is carried out in the absence of an energy source other than said precursors.

2. An in vitro method for producing a polypeptide, which comprises the steps of:

(a) reacting an amino acid with a nucleic acid adaptor molecule which comprises tRNA in the presence of aminoacyl-tRNA synthetase to obtain a precursor comprising an amino acid and said nucleic acid adaptor; and (b) condensing the precursor in an aqueous solution in the presence of an effective amount of ribosomes or a larger ribosomal subunit, and in the presence of an effective amount of aromatic tertiary amine under conditions which allow for the production of a polypeptide, wherein substantially all of the soluble protein factors are removed from the aqueous solution and where the condensing is carried out in the substantial absence of an energy source other than said precursor.

3. A method for producing a polypeptide according to claim 1 or 2, wherein the condensation of the precursors is carried out in the presence of a template molecule comprising a nucleic acid and wherein said template molecule interacts with the adaptor molecule.

4. A method for producing a polypeptide according to claim 3, wherein the aromatic tertiary amine compound is a member selected from a group consisting of (a) a pyridine compound of the formula I:

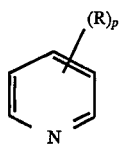

wherein R independently represents a member selected from a group of a hydrogen atom, a halogen atom, a $C_1$–$C_4$ aliphatic hydrocarbon group, an amino group, a $C_5$–$C_8$ alicyclic hydrocarbon group, a $C_6$–$C_{10}$ aromatic hydrocarbon group, a hydroxyl group, a sulfhydryl group or a heterocyclic group having at least one hetero atom, all of which except the hydrogen atom and the halogen atom may be optionally substituted; alternatively R represents a group of a formula: —COQ, wherein Q represents a hydrogen atom, a $C_1$–$C_4$ aliphatic hydrocarbon group, an amino group, a $C_5$–$C_8$ alicyclic hydrocarbon group, a $C_6$–$C_{10}$ aromatic hydrocarbon group, a hydroxyl group, a sulfhydryl group or a heterocyclic group having at least one heteroatom, all the groups of which may be optionally substituted; and p represents an integer of 1 to 5;

(b) an imidazole compound of the formula II:

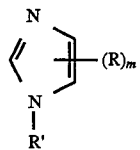

wherein R is the same as defined above; R' represents the same atoms or groups with those given in R provided that it excludes a halogen atom, an amino group, a hydroxyl group and a sulfhydryl group, and those atom and groups are also excluded in Q; R and R' are independent from each other; and m represents an integer of 1 to 3;

(c) a purine base compound represented by the formula III:

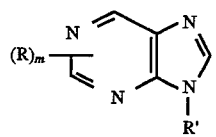

wherein R and R' are the same as defined above and independent from each other, and m represents an integer of 1 to 3, or the formula IV:

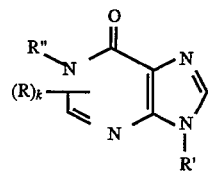

wherein R and R' are the same as defined above; R" represents the same atoms or groups with those given in R provided that it excludes a halogen atom, an amino group, a hydroxyl group and a sulfhydryl group, and those atom and groups are also excluded in Q; R, R' and R" are independent from each other; and k represents an integer of 1 or 2; and (d) a pyrimidine base compound represented by the formula V:

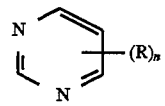

wherein R is the same as defined above and n represents an integer of 1 to 4, the formula VI:

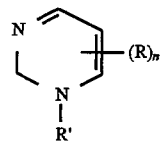

wherein R, R' and n are the same as defined above and R and R' are independent from each other; or the formula VII:

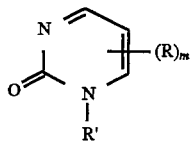

wherein R and R' are the same as defined above and independent from each other; and
m represents an integer of 1 to 3.

5. A method for producing polypeptides according to claim 4, wherein R represents a hydrogen atom, a methyl group, an amino group and a dimethylamino group, and R' and R" represent independently a hydrogen atom, a methyl group, a ribosyl group, a deoxyribosyl group, a 5'-monophosphoribosyl group, a 5'-monophosphodeoxyribosyl group, 5'-diphosphoribosyl group or a 5'-diphosphodeoxyribosyl group.

6. A method for producing polypeptides according to claim 4, wherein the pyridine compound is α-picoline, β-picoline, γ-picoline, 2-aminopyridine, 3-aminopyridine, 4-aminopyridine or 4-dimethylaminopyridine; the imidazole compound is imidazole or 1-methylimidazole; the purine compound is guanine, purine, adenine, 9-methyladenine, 7-methyladenine, adenosine, 2'-deoxyadenosine, adenosine 5'-monophosphate or adenosine 5'-diphosphate; and the pyrimidine compound is cytosine, uracil, thymine, cytidine, 2'-deoxycytidine, cytidyl 5'-monophosphate, and cytidyl 5'-diphosphate.

7. The process according to claim 3, wherein the template molecule is a mRNA of interest or variant thereof.

8. The process according to claim 3, wherein the template molecule is polyuridylic acid, polyadenylic acid or a block copolymer thereof.

9. The process according to claim 3, wherein the template molecule is a nucleic acid that codes for a protein of interest.

10. The process according to claim 3, wherein the reaction temperature is 0° C. to 90° C.

11. The process according to claim 7, wherein the condensation of the precursors is carried out at a pH of 5 to 11.

12. The process according to claim 8, wherein the condensation of the precursors is carried out in the presence of cations selected from a magnesium ion and at least one cation selected from a potassium ion and an ammonium ion.

13. The process according to claim 1 or 2, wherein substantially all of said energy source has been removed prior to condensing of the precursor.

14. The process according to claim 1 or 2, wherein substantially all ATP and GTP are removed prior to condensing of the precursor.

* * * * *